Figure 1:
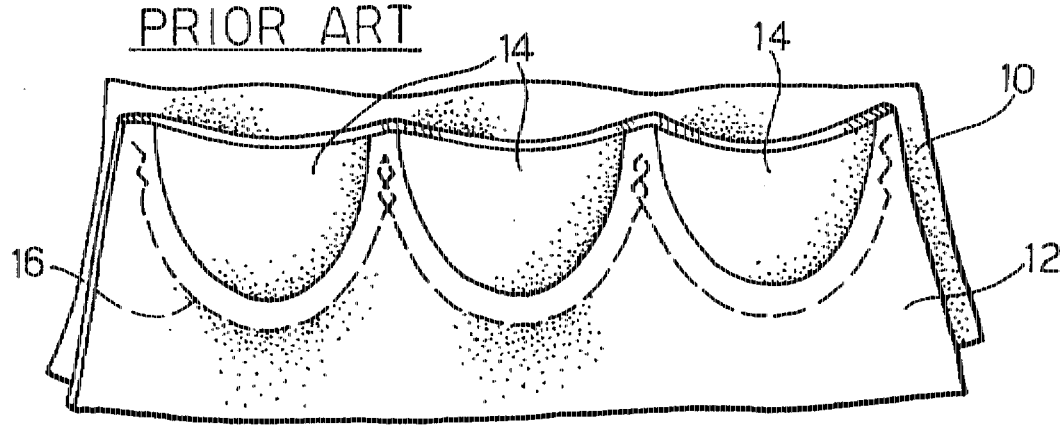

United States Patent [19]
Vallana et al.

[11] Patent Number: 5,713,953
[45] Date of Patent: Feb. 3, 1998

[54] CARDIAC VALVE PROSTHESIS PARTICULARLY FOR REPLACEMENT OF THE AORTIC VALVE

[75] Inventors: Franco Vallana, Turin; Maria Curcio, Saluggia; Carla Stacchino, Turin; Stefano Rinaldi, Parma, all of Italy

[73] Assignee: Sorin Biomedica Cardio S.P.A., Turin, Italy

[21] Appl. No.: 601,970

[22] Filed: Feb. 15, 1996

Related U.S. Application Data

[63] Continuation of Ser. No. 142,899, Oct. 22, 1993, abandoned, which is a continuation of Ser. No. 886,602, May 20, 1992, abandoned.

[30] Foreign Application Priority Data

May 24, 1991 [IT] Italy .................... TO91A0388

[51] Int. Cl.⁶ .................................................. A61F 2/24
[52] U.S. Cl. .................................................. 623/2
[58] Field of Search ............................. 623/1, 2, 3, 11, 623/66, 900

[56] References Cited

U.S. PATENT DOCUMENTS

| | | | |
|---|---|---|---|
| 3,320,972 | 5/1967 | High et al. | 623/2 |
| 3,736,598 | 6/1973 | Bellhouse et al. | 623/2 |
| 4,291,420 | 9/1981 | Reul | 623/2 |
| 4,510,628 | 4/1985 | Kolff | 623/2 |
| 4,624,822 | 11/1986 | Arru et al. | 623/2 X |
| 4,725,274 | 2/1988 | Lane et al. | 623/2 |
| 4,770,665 | 9/1988 | Nashef | 623/2 |
| 4,787,901 | 11/1988 | Baykut | 623/2 |
| 4,996,054 | 2/1991 | Pietsch et al. | 623/2 X |
| 5,080,670 | 1/1992 | Imamura et al. | 623/2 |
| 5,156,621 | 10/1992 | Naula et al. | 623/2 |
| 5,197,979 | 3/1993 | Quintero et al. | 623/2 |
| 5,352,240 | 10/1994 | Ross | 623/2 |

FOREIGN PATENT DOCUMENTS

| | | | |
|---|---|---|---|
| 0133420 | 8/1985 | European Pat. Off. | 623/2 |
| 0155245 | 9/1985 | European Pat. Off. | 623/2 |
| 0275535 | 7/1988 | European Pat. Off. | |
| 2355959 | 6/1975 | Germany . | |
| 2822464 | 12/1978 | Germany . | |
| 1477643 | 6/1977 | United Kingdom . | |
| 1599407 | 9/1981 | United Kingdom . | |

*Primary Examiner*—David Isabella
*Attorney, Agent, or Firm*—Robert D. Schaffer; Rogers & Wells

[57] ABSTRACT

A stentless prosthesis is made completely from material, for example bovine pericardium, other than valve material. A projection of the valve sleeve allows reparatory operations on surrounding tissues.

13 Claims, 5 Drawing Sheets

CARDIAC VALVE PROSTHESIS PARTICULARLY FOR REPLACEMENT OF THE AORTIC VALVE

This is application of U.S. patent application Ser. No. 08/142,899, filed Oct. 22, 1993, now abandoned, which is in turn, a continuation of application Ser. No. 07/886,602, filed May 20, 1992, now abandoned.

DESCRIPTION

The present invention relates to cardiac valve prostheses or, briefly, artificial cardiac "valves".

In the traditional approach, these artificial valves can essentially be separated into two basic categories, that is to say:

the so-called "mechanical" valves, in which the blood flow through the valve is controlled by one or more obturators constituted by rigid bodies (for example, a lenticular core of graphite coated with biocompatible carbonaceous material) mounted so as to be able to oscillate in a respective annular stent or armature of rigid material (for example, titanium), and the so-called "biological" valves in which the blood flow is controlled by valve leaflets in constituted by biological tissue mounted on a rigid, or only slightly flexible, stent or armature.

The valve leaflets question can be those of a natural cardiac valve taken from an animal (for example, a natural pig's valve) and mounted on the stent after treatment (stabilisation) to render it biologically inert.

In other solutions, however, the biological tissue utilised to form the valve leaflets is biological tissue other than valve tissue (for example, bovine pericardium).

A prosthesis of this latter type is described in European patent EP-B-0155245.

Figure 6:
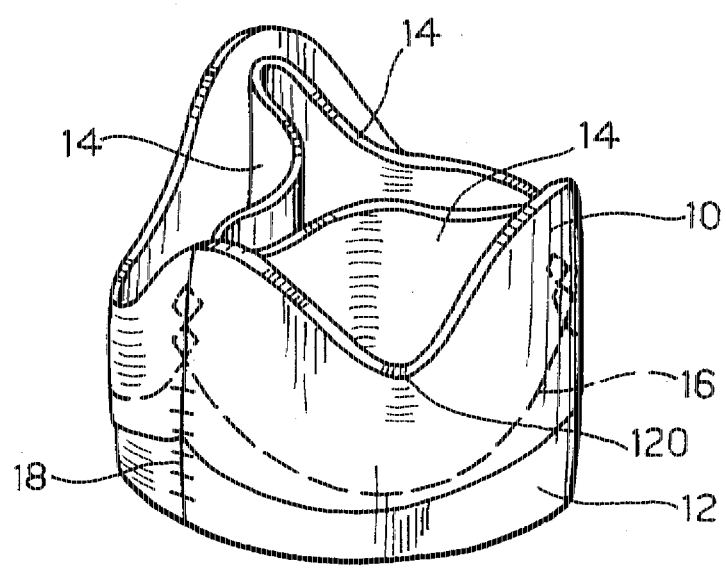

This prior patent describes a cardiac valve prosthesis comprising an armature (or stent) of substantially rigid material of annular form within which is fitted a valve sleeve of biological tissue constituted by two sheets of biological material (for example, animal pericardial tissue) treated to render it biologically inert: in particular, the said sleeve, indicated 10, is illustrated on its own in FIG. 6 of the drawings accompanying the patent.

Figure 2:
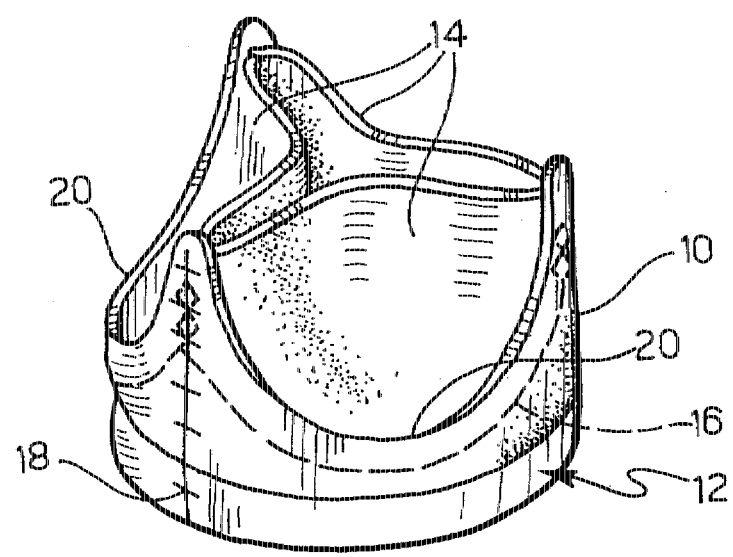

In this known solution, the sleeve in question is obtained by the technique illustrated schematically in FIGS. 1 and 2 of the appended drawings.

In FIG. 1, two sheets of biological material (for example, bovine pericardium) which have undergone a fixation in glutaraldehyde are indicated 10 and 12 respectively.

The first sheet 10, intended to constitute the outer portion of the valve sleeve of an aortic valve prosthesis, has an approximately rectangular shape, whilst the other sheet 12, intended to constitute the internal or functional part of the valve sleeve (or rather, in practice, the valve flaps) also generally rectangular. However, the sheet 12 has previously been subjected to a shaping process intended to give it three shaped portions 14 of approximately semi-circular, or half-moon, shape with arcuate edges and with a generally pocket or fingernail shape such that when the valve sleeve is closed into a tube (FIG. 2), the leaflets or flaps 14 thus formed project in a convergent manner towards the internal orifice of the prosthesis.

A detailed description of a process and of apparatus used for performing this shaping operation is provided in European patent EP-B-0133420 as follows:

This process allows valve flaps of biological tissue for cardiac prostheses to be made economically with characteristics of high reliability and durability.

The deformed shape in which the biological tissue of each flap is finally fixed is, in fact, that in which the flap itself is mounted in the prosthesis. In other words, since the fixation is effected in a deformed shape the valve flap stably assumes this deformed shape and tends spontaneously to return to this latter even after having been stretched from this shape under the action of the flow of blood.

The process of the invention therefore allows a precise shaping of the valve flaps before assembly in the prosthesis.

It is moreover possible to perform the shaping of the valve flaps whilst the flaps themselves are subjected to a pressure range which substantially reproduces the pressure range to which the flaps are subjected in use. In particular, in prostheses provided with several valve flaps it is possible to impart to the flaps themselves, upon final fixation of the biological tissue, a mutually matching configuration which can be exactly reproduced in the conditions of use.

With the process according to the invention, then the risk of deformation stresses being imparted to the biological tissue is completely eliminated, particularly in the region of connection to the frame. The biological tissue is in fact mounted (sewn) to the frame after having been finally fixed and shaped in the final conformation of use. With shaping under fluid pressure the intrinsic disadvantages of mechanical shaping by stamping are also avoided.

In the implantation position the prosthesis is sutured to the cardiac wall in the zone surrounding the orifice formed by removal of the autologous valve membranes.

Structurally, the prosthesis is constituted by a support structure (frame) of generally annular form, which is intended to be sutured to the cardiac wall and to receive within it a valve sleeve including valve flaps of biological tissue. As is known to the expert in the art and as will be better illustrated below, the prosthesis is intended to be traversed by a flow of blood to prevent the flow of blood in the opposite direction.

The stent and the projections are normally constituted by a single piece of biocompatible material such as, for example, titanium, a chrome-cobalt alloy or one based on cobalt, or else the plastics materials known by the commercial names "Teflon" or "Delrin", these being registered trade marks.

The stent and the projections are encased in a biocompatible textile such as, for example, a textile made with the yarn mold under the trademark "Dacron".

The textile forms, on the outer face of the stent, a wide annular loop constituting a ring for the suture of the prosthesis to the cardiac tissue.

Within the loop there is normally provided an annular pad of biocompatible material, constituting a reinforcing core for the suture ring of the prosthesis. The pad is constituted by a ring of fabric which can easily be traversed by the surgical thread utilised for the suture of the prosthesis to the cardiac tissue.

The textile is wound around the stent and subsequently closed in a generally tubular configuration by suture stitches.

Other arrangement for achieving the same final result are naturally possible.

To the textile, and possibly also on the thread constituting the suture stitches, there is applied (before or after mounting on the stent) a coating of biocompatible caronaceous material constituted, for example, by graphite, glassy carbon or carbon having a turbostratic structure.

The coating, which significantly improves the antithrombogenic properties of the textile, is applied by cathodic spraying (sputtering) utilising a target constituted by a carbonaceous material, normally selected from the group comprising graphite, glassy carbon and carbon with a turbostratic structure.

The application by cathodic spraying is described in a detailed manner in EP-A-0 102 328 by the same applicant, the description of which is incorporated herein by reference. The application of the coating by cathodic spraying can be effected at a temperature close to ambient temperature, avoiding damage to the textile or the material of the stent in the case in which the coating is applied after the textile has been fixed to the stent.

The interior part of the prosthesis is occupied by a valve sleeve of biological tissue including three valve flaps.

The sleeve is made of an inert biological material. Biological tissues which have been used with success are cow or pig pericardium tissues, although the use other nature and origin is other nature and origin is not excluded. For example, it has been proposed to utilise as biological tissue a membrane of cranial or cervical dura mater taken from animals, or even a membrane of human or animal fascia lata.

After removal, the biological tissue is subjected to a cleaning operation. Subsequently there is effected a selection of the tissue with the intention that only the structurally most homogeneous and suitable parts of it are to be retained.

The selected layers of biological tissue are then subjected to a treatment operation intended to stabalise the elastic and mechanical strength thereof and to confer on them characteristics of chemical inertness with respect to blood.

These operations, generally known as "fixation" or "stabilisation" operations, are normally performed by immersing the tissue in solutions of glutaraldehydes with controlled pH, possibly enriched with anticalcifying additives.

The fixation operation generally involves the formation of stable cross links between the various forms of the glutaraldehyde and the amine groups of the proteins constituting the collagen of the tissue.

The treatment times can vary widely in dependence on the characteristics of the biological tissue subjected to the fixation and the manner in which the fixation operation is performed. During the course of the treatment process, the concentration of the fixation solution is varied. For example, in the case in which solutions of glutaraldehyde are used, an initial phase, the said prefixation, is performed with a solution of glutaraldehyde in a concentration of the order of 0.2% which increases to a final fixation phase in which the concentrations are of the order of 0.5%.

For the purpose of understanding the invention it is necessary to distinguish between an incompletely fixed biological tissue (that is to say, a tissue subjected only to prefixation) and a completely fixed biological tissue. The incompletely fixed tissue in fact retains characteristics of plastic deformability which allow shaping operations to be performed thereon. The finally fixed tissue on the other hand has different elastic characteristics such that, after a possible deformation, the tissue tends to return spontaneously to the conformation assumed upon fixation.

As can be seen, the sleeve in the assembled configuration of the prosthesis and in open development, the sleeve is constituted by two layers of biological tissue one of which (inner layer) constitutes the sleeve proper and is provided with shaped parts constituting valve flaps. The other layer of biological tissue (outer layer), indicated, constitutes a tubular support covering for fixing the sleeve to the frame. For this purpose, in correspondence with the valve flaps the layer has crescent shape notches the shape of which reproduce in development the shape of the sides of the projections of the stent of the prosthesis frame.

The two biological tissue layers constituting the sleeve are sutured together with surgical thread along suture lines, preferably of the zig-zag type, which extend along crescent shape paths and each of which defines a crescent shape edge of a respective valve flap. Preferably the thread utilised for the suture lines is provided with a coating of biocompatible carbon material described with reference to the textile.

In a manner which will be described in more detail below the valve flaps have imparted to them a general bowl-shape configuration the concavity of which faces the layer.

Consequently, when the two layers of biological tissue sutured together are wound into a tube by suturing together two opposite edges of the layers along a line of stitching indicated, the free edges of the valve flaps indicated converge towards the interior of the sleeve, being arranged in a closely matching star shape configuration.

As can be seen, the sleeve has a generally frusto-conical configuration which, although not essential, has been found to be preferable for the functional purposes of the prosthesis.

The mounting of the sleeve on the frame is normally effected by suturing the layer onto the cladding textile along the end edges of the frame and the projections.

On the opposite side of the free edges of the a valve flaps the inner layer of the sleeve is provided with a terminal portion which extends beyond the corresponding end edge of the layer and can be turned inwardly of the frame and be sutured to the textile adjacent the inner edge of the suture ring.

The conformation of the sleeve and its disposition upon assembly within the frame are such that substantially the whole of the surface of the prosthesis intended to be invested with the blood flow is covered with biological material having significant antithrombogenic properties.

Making reference, by way of example, to an atrioventricular implantation arrangement, in the diastolic phase the blood which flows out of the atrium enters the ventricle and traverses the prosthesis. In this direction of flow the blood flows over the convex face of the valve flaps separating their free edges and forming a substantially cylindrical central aperture in the prosthesis body, through which the blood can flow freely.

As soon as a pressure difference sufficient to cause the blood to flow in the opposite direction is established across the prosthesis by the effect of the contraction of the ventricle, the pressure extorted by the blood itself on the concave faces of the valve flaps forces the free edges into the closely matching position. In these conditions the blood flow across the prosthesis is prevented.

The apparatus includes a reservoir intended to receive a solution for the fixation of the biological tissue. The reservoir has a generally drum-shape configuration and is constituted by a tubular peripheral wall the openings at the ends of which are closed by a cover and by a bottom wall constituted by plate elements of circular form. Between the cover and the bottom wall are interposed the elements which tightly hold the cover and the bottom wall onto the peripheral wall ensuring fluid-pressure tight sealing of the reservoir.

The fixing solution is taken from a collection reservoir and conveyed into the reservoir by means of a pump through a duct provided in the bottom wall of the reservoir. Between the pump and the duct there is interposed a valve intended to prevent the return of the solution towards the collection reservoir when, as is described in greater detail below, the solution contained in the reservoir is put under pressure.

The fixation solution introduced into the reservoir is in general a solution intended to perform the final fixation (terminal fixation) of a biological tissue, for example a 0.5% solution of glutaraldehyde.

In general, the reservoir is not completely filled with the solution. Above the free surface of the solution there is thus defined a chamber into which a gas under pressure derived from a source constituted, for example, by a gas bottle can be admitted through an aperture provided in the side wall of the reservoir.

In the connection pipe between the source and the chamber there is interposed a pressure regulator which allows regulation of the gas pressure in the chamber and, consequently, of the hydrostatic pressure of the solution within the reservoir.

In the cover of the reservoir there are provided threaded apertures, each of which constitutes a seat for mounting a forming element.

In the cover there is normally provided a plurality of apertures, which represent a section of the reservoir taken on a diametral plane of the reservoir itself. The apertures are distributed around a circular track concentric with the peripheral wall of the reservoir. Each communicates through a respective radial duct extending through the cover with a collection cavity formed in a central position in the wall of the cover. The cavity communicates with the suction side of a pump the delivery side of which is connected to a breather duct which opens into the interior of the collection reservoir.

Each forming element is substantially constituted by a frusto-conical body having a tubular structure, supported at its larger base by a sleeve body externally threaded at. The inner cavity of the sleeve body communicates with the inner cavity of the frusto-conical body. In the assembly disposition of the elements in the reservoir the sleeve body of each element is screwed into the associated aperture in such a way that the tubular body supported by it projects into the interior of the reservoir so as to be substantially immersed in the fixing solution when the reservoir is filled.

At the end facing outwardly of the reservoir each aperture is closed by an insert of transparent material (for example plexiglass) which allows the interior of the frusto-conical body of the forming element screwed into the aperture to be observed from the outside.

The tubular body of each forming element has an intermediate body portion with three apertures angularly adjacent one another and separated by shaped wall elements extending axially with respect to the body itself. Each element has a generally flattened form in the radial direction with respect to the body, with a biconvex symmetrical shape. On the side facing outwardly of the body, each element is delimited, for reasons which will be illustrated better below, by a rounded surface free from sharp corners or other discontinuities.

At the end facing the sleeve body each aperture has a terminal edge the shape which reproduces the shape of the crescent-shape edges of the valve flaps.

On the outer surface of the tubular body above and below the apertures respectively, there are provided annular grooves the function of which will be illustrated below.

The apertures and the grooves are normally formed by mechanical working of the forming element which is constituted by a single piece of plastics material such as the materials sold under the trademarks "Teflon" or "Delrin".

The diametral dimensions of the frusto-conical body of each forming element are substantially identical with the diametral dimensions of the sleeves which it is intended to make.

In use of the apparatus, sheets of incompletely fixed biological tissue, (that is to say sheets of biological tissue subjected only to the prefixation operation) are formed into a tube by suturing together two opposite edges of the sheet itself so as to form tubular sheaths of frustoconical form which can be fitted over the bodies of the elements.

Only the portion of the forming element comprising the body portion with the apertures is illustrated. The dimensions of the sheath are chosen in such a way that each sheath forms, with respect to the corresponding forming body a loose coupling.

After having been fitted onto the forming body each sheath is securely fixed onto the forming element, for example by means of two resilient seals of the type usually called "O rings" which engage the grooves. The suture line along which the sheath has been closed into a tube is positioned in correspondence with one of the wall elements.

The sheath is thus fitted with a fluid tight seal onto the associated body in an arrangement in which the sheath portions extending across the apertures constitute diaphragms which separate the internal cavities of the tubular body from the exterior of the forming element.

Normally, the sheaths are mounted on the forming bodies with the elements fixed to the cover of the reservoir remote from the reservoir itself.

After having fitted the sheaths onto the elements and before finally locking the cover onto the reservoir body, the pump can now be activated for a short time in such a way as to create a vacuum within the cavities of the forming elements. Under the suction of this vacuum the sheath portions extending through the apertures are, so to speak, "sucked" into the interior of the forming bodies. The deformed conformation thus assumed by such sheath portions can be seen through the transparent insert. It is thus immediately possible to detect the presence of defects (for example non-uniformity) and errors in mounting the sheaths in such a way as to be able to replace defective sheaths and eliminate such mounting errors before proceeding to the shaping and fixation treatment of the biological tissue.

To effect such treatment the cover carrying the elements on which the sheaths are sealingly fitted is closed over the reservoir. The pump is now activated making the fixation solution flow into the interior of the reservoir. The level of the solution is regulated in such a way that the whole of the sheath is immersed in the fixation solution. Preferably, a small quantity of solution is also introduced into the interior of the forming bodies in such a way as to act on the inner surface of the sheath.

After having closed and sealed the reservoir the supply source and the pressure regulator are activated in such a way as to establish a controlled pressure within the solution.

The pump remains inoperative so that the inner cavity of each forming body is practically at atmospheric pressure. Consequently, the pressurisation of the solution within the reservoir is such that a pressure differential is established across the apertures, which causes deformation of the portions of the sheath covering the apertures. The fixation solution acts on such sheath portions to dilate them and press them into the tubular body in a disposition in which, the median parts of such portions are positioned in mutual contact with a star-shape geometry substantially similar to the valve flaps.

Naturally, the resistance afforded by the tissue of the sheath to the pressure exerted by the fixation solution varies in dependence on the nature of the biological tissue, on its thickness and the dimensions of the apertures. The gas pressure within the interior of the chamber, which determines the pressure of the solution, is regulated in such a way as to bring the deformed portions of the sheath to a configuration of mutual matched shaping substantially similar to that of the valve flaps of the sleeve.

The instantaneous configuration reached by the deformed portion of the sheath can be observed by an operator through the transparent inserts. It is therefore possible gradually to increase the pressure of the fixation solution until the configuration of mutual shape matching is positively achieved.

Each deformed portion of the sheath then has a general bowl-shape configuration and is delimited on one side by a crescent-shape edge the shape of which reproduces the shape of the terminal edge of the aperture and, consequently, the crescent-shape edge of one of the valve flaps. In other words, in each of the portions there is formed a shaped element of stably fixed biological tissue the conformation of which is exactly similar to the conformation of one of the valve flaps of the sleeve.

The pressure difference which produces the deformation of the sheath is maintained for the period necessary to produce complete fixation of the biological tissue of the sheath by the solution.

The biological tissue intended to constitute the sleeve, and in particular the valve flap, is subjected to a shaping operation which makes it assume the final conformation of use when the tissue is still not completely fixed. The final or complete fixation is effected when the biological tissue has already been deformed making it assume the final conformation of use.

In this way the fixed biological tissue tends to reassume, after any accidental deformation, the conformation in which the tissue was mounted in the prosthesis in the form of a valve flap.

Moreover, the existence of a pressure gradient across the deformed portions of the sheath encourages the diffusion of the fixation solution across the biological tissue ensuring an intimate penetration thereof into the tissue. This also allows the treatment times necessary to obtain final fixation of the tissue to be significantly reduced.

The effect of the pressure gradient which is established across these deformed portions is that the solution in fact seeps through the biological tissue, penetrating into the tubular body of the forming element.

The duration of the fixation operation can be chosen in dependence on the pressure at which the solution is delivered (that is to say, in dependence on the pressure gradient applied across the two faces of each portion of the sheath extending across one of the apertures) in such a way that the deformed portions of the sheath are intimately permeated by the solution.

Further, the fact that the portions of the sheath intended to constitute the valve flaps of the sleeve assume their final conformation under the action of a fluid under pressure permits the shaping of such flaps whilst the flaps themselves are subjected to a pressure range which substantially reproduces the pressure range to which the flaps are subjected in use. In this way, upon final fixation of the biological tissue, there is obtained a mutual shape matching configuration between the flaps which can be exactly reproduced in the conditions of use. This also avoids the possibility of non-uniform stresses and strains arising in such portions which could prejudice the correct operation of the prosthetic valve flaps. The conformation of the wall elements and, in particular, the presence of the rounded surfaces on the radially outer side of each element avoids the possibility of stress phenomena or lesions arising during the shaping and final fixation operation in the regions of biological tissue stretched out over the elements, such as would prejudice the strength of the tissue.

In the preceding part of the description, explanation has been given with reference to a situation of use of the apparatus in which the pressure gradient applied between the opposite faces of each of the portions of biological tissue defining the valve flaps is exclusively derived from the pressure applied to the fixation solution within the reservoir. It is, however also possible to establish the said pressure gradient by the effect of a combined action of the pressure applied to the fixation solution and the vacuum created within the cavity of each shaping element by the pump. In this case the pump, which allows (as previously described) a preliminary control of the structural characteristics and the exact positioning of the sheaths mounted on the shaping elements, is also activated during the final fixation operation on the biological tissue, by jointly adjusting the effect of pressurisation of the solution by the gas taken from the source and the degree or vacuum generated within the shaping elements by the pump.

It is also possible to envisage the use of apparatus in which the pressurisation system formed by the gas source and the regulator is eliminated. In this case the pump is activated both to perform a preliminary check on the structural characteristics and exact positioning of the sheaths mounted on the shaping elements, and to generate, after the reservoir has been filled with the fixation solution, the pressure gradient which determines the deformation of the portions of biological tissue extending across the apertures.

In structural terms, the said gradient can be established in at least three different ways, that is to say:

i) by applying (for example by means of gas taken form the source) a pressure to the fixation solution within the reservoir, maintaining the internal cavities of the forming elements substantially at atmospheric pressure, ii) by applying the said pressure to the fixation solution and simultaneously creating (for example by operation of the pump) a vacuum (a pressure less than atmospheric pressure) in the interior cavity of the forming elements, and iii) exclusively by the effect of the vacuum created in the interior cavities of the forming elements, whilst the solution is maintained at substantially atmospheric pressure.

Upon completion of the fixation operation, the sources which caused the said pressure gradient are de-activated and the cover is removed from the reservoir. The sheaths can then be disengaged from the forming elements by removing the sealing rings.

After the removal of the stitches previously applied to effect the closure into tubular form, the sheet constituting each sheath is again opened out, assuming the conformation in which the sheet of biological material, initially flat, now has three bowl-shaped parts substantially equal to one another and delimited on corresponding sides by crescent shape edges constituting the crescent edges.

In other words, the sheet of biological tissue obtained starting from the sheath subjected to the final fixation treatment incorporates a valve sleeve provided with three completely formed and shaped flaps.

The separation of the biological tissue of the sheath along a line which joins the ends of the crescent shaped edges permits the separation of the frusto-conical sleeve from the remaining part of the sheath intended to be discarded, forming the free edges of the valve flaps.

The separation of the biological tissue of the sheath is effected after the sheath has been released from the forming element and returned to an open position. It is, however, possible to effect separation of the sheath when it is still closed in the form of a tube, possibly when it is still fitted into the forming element.

The valve sleeve is subsequently mounted on the prosthesis.

The two sheets 10 and 12 are then connected together by a line of stitching 16 (for example, with Dacron thread coated with biocompatible carbonaceous material) which extends closely adjacent the outer peripheries of the half-moon portions forming the valve leaflets 14 and therefore has a festoon-like course.

As already mentioned, the two sheets 10 and 12 connected together by the festoon-like line of stitching 16 are then closed into a tube and connected together along their facing edges by means of a further line 18 of stitching. All this gives rise—after mounting on the stent—to the structure illustrated schematically in FIG. 2, in which the three valve leaflets are able, alternately, to move apart so as to allow the blood to flow in one direction (upwardly with reference to FIG. 2) and to fit together under the action of the blood pressure so as to prevent the blood from flowing in the opposite direction.

All this accords with criteria widely known in the art and which do not require to be explained further herein.

Preferably, the stitch line 18 is located at one of the so-called commissural faces (that is, the zone of maximum axial extent) of the sheets 10 and 12.

In addition, the extreme edge of the outer sheet 10 intended to be situated downstream in the implanted position of the valve (that is, the extreme edge of the outer sheet 10 intended to face the output side of the valve) is slit, usually before closure of the tube, very close to the festoon stitch line 16, and thus very close to the arcuate edges of the valve flaps 14, so as to form an output edge 20 intended in turn to allow the valve sleeve to be fixed to the valve stent. In this respect one may again refer to the specification of European patent EP-B-0155245 asx follows:

The stent is constituted by a single piece of biocompatible material such as, for example titanium, chromium-cobalt alloys or cobalt based alloys, or even the plastics materials known by the trade names "TEFLON" or "DELRIN". When the stent is made from plastics material an annular metal insert is normally embedded therein to allow the prosthesis to be located radiologically after implant in the patient.

The wall of the stent has apertures some of which are generally indicated form a ring, these apertures which opening into the tubular portion of the stent in a generally circular path lying in a plane parallel to the general plane of the end edge. Alternatively the apertures may be arranged along a path which follows the undulate profile of the edge.

Other apertures indicated, however, pass through the appendages near their free ends. In particular, each appendage has a pair of apertures aligned longitudinally relative to the appendage itself.

A covering of biocompatible textile, for example the textile known by the tradename "Dacron Fabric" is generally indicated and wraps the stent entirely.

The structure of the covering, is a type of stocking or knitting which covers the frame.

The covering is constituted essentially by two shaped sheets of biocompatible Dacron fabric.

The first sheet is intended to be applied to the outer surface of the stent so as to cover the portion of this surface approximately between the ring of apemares and the end edge.

The first sheet, normally made from a tubular knitted Dacron thus has a general shape which reproduces the shape of the outer surface of the stent save only for its smaller axial extent.

The second sheet, is also made from a knitted Dacron and has instead an axial extent which is much greater than that of the stent. It thus includes a so-called lower portion the shape of which reproduces approximately the shape of the inner surface of the stent, and an upper end portion generally indicated which can be turned over in the form of a collar outwardly of the frame.

The portion of the second sheet forms a wide annular loop on the outer face of the stent, defining a ring for the suturing of the prosthesis to be cardiac tissues.

Within the loop is an annular cushion of biocompatible material which forms a stiffening core for the suture ring of the prosthesis. The cushion is constituted by a ring of textile through which the surgical thread used for the suturing of the prosthesis to the cardiac tissue can easily be passed.

The covering is closed by the connection of the first and second sheets and fixed to the stent by the suture stitches.

In particular, the suture stitches connect the first sheet and the second sheet along respective facing edges along the downstream edge of the stent.

The stitches indicated, however, extend through the apertures connecting the regions of the first sheet and the second sheet which face each other at the opposite ends of these apertures.

The stitches indicated also extend through the apertures connection the regions of the sheets facing each other at the two ends of the apertures. The suture stitches extend further outwardly of the frame of the prosthesis, being connected to the upper edge of the first sheet, that is to say the edge of the first sheet facing the apertures, the end edge of the portion of the second sheet forming the loop. The stitches are connected to the end edge of the loop to which further stitches are connected which close the loop around the cushion.

The assembly formed by the stem covered by the biocompatible covering constitutes the supporting structure or frame of the prosthesis for receiving within it the sheets of biological material defining the valve flaps.

Preferably the covering textile and the thread used for the suture stitches is coated (before or possibly even after assembly on the stent) with a coating of biocompatible carbonaceous material.

This coating serves the function of at least partially inhibiting reactions which are at the root of thrombogenic processes and the uncontrolled growth of natural tissues around the prosthesis.

Indeed, although a small growth of natural tissue in the region in which the suture ring is applied to the cardiac wall is considered beneficial for the better anchoring of the prosthesis, anomalous growth of tissue in the region inside the frame could alter the blood flow conditions through the prosthesis, causing a deterioration in its operating characteristics until it is unnecessary to replace it.

Consequently, although it is possible to apply it over the whole surface of the textile, the carbonaceous coating is preferably applied while leaving uncovered, for example, a portion of suture ring over which the blood will not flow in the implanted position of the prosthesis.

Thus the growth of natural tissues is allowed in the zones in which this growth is beneficial and on the other hand is opposed where this phenomenon would have harmful effects with regard to the operational efficiency of the prosthesis.

The coating of biocompatible carbonaceous material is applied by cathode sputtering with the use of a target constituted by a carbonaceous material selected from the group consisting of graphite, glassy carbon and carbon with a turbostratic structure.

The application of a carbon-based biocompatible material by cathode sputtering is described in detail in the European Patent Application published under the number 0102328 in the name of the same applicants. The application of the coating by cathode sputtering may be carried out at temperatures close to the ambient temperature, thus avoiding damage to the textile or to the stent material, when the coating is applied to the textile after its fixing to the stent.

Within the axial orifice of the frame of the prosthesis is a valve sleeve.

The sleeve is constituted by two sheets of inert biological material. Biological tissues constituted by cattle or pig pericardial tissues may be used successfully for the manufacture of the sleeve although the use of biological tissues of different types and origins is not excluded. For example it has been proposed to use a membrane of cranial or cervical dura mater or even membranes of fascia lata taken from man or animals as the biological tissue.

After removal, the biological tissue is subjected to a cleaning operation. Subsequently it is subjected to a selection so as to keep only those parts which are structurally most homogeneous and suitable.

The sheets of biological tissue selected are then subjected to a treatment for stabilising their elastic properties and mechanical strength and to give them characteristics of chemical inertness to blood.

This operation, generally known as "fixation" or "stabilisation" is normally carried out by the immersion of the tissue in solutions of glutaraldehyde having a controlled pH, possibly enriched with anti-calcifying additives. The fixation operation in general results in the formation of stable cross links between the various forms of the glutaraldehyde and the amine groups of proteins constituting the cologen of the tissue.

The treatment times may vary widely in accordance with the characteristics of the biological tissue subjected to fixation and the manner in which the fixation is carried out. During the treatment, the concentration of the fixation solution is varied. For example, when glutaraldehyde solutions are used, after an initial, so-called prefixation stage, carried out with a 0.2% solution of glutaraldehyde, the solution is changed to concentrations of the order of 0.5% for the final fixation stage.

The biological tissue may be fixed finally before it is cut and shaped for the sheets constituting the sleeve. However it is also possible to use non-fixed biological tissue, or tissue subjected solely to the initial stage in the fixation process for the manufacture of the sleeve, particularly with regard to the sheet. In particular it is possible to shape the sheet by using a pressure gradient generated in the fixation liquid for this purpose.

For an understanding of the present invention it will suffice to note that the valve sleeve is constituted essentially by two shaped sheets of biological tissue closed into a tube by suture stitches along opposing end edges of the two sheets. Consequently the two sheets closed into a tube are at least partly fitted one within the other. For this reason, in the description below, the two sheets are identified generally as the radially outermost sheet and the radially innermost sheet. The radially outermost sheet constitutes essentially a support band for the fixing of the sleeve to the frame of the prosthesis.

It thus has a shape substantially identical to that of the internal face of the stent covered by the covering.

In the assembled position of the prosthesis the outer sheet of the sleeve is fixed to the inner sheet of the covering by suture stitches stitched through the end edge of the inner sheet extending so as to cover the edge of the stent and the margin of the sheet facing it.

The suture stitches are preferably located along the margin of the outer sheet which faces slightly outwardly of the frame. This is in order to avoid the inner sheet of the sleeve coming into contact with the stitched region itself during operation of the prosthesis, with the risk of wear. The arrangement described means that during operation the surface of the inner sheet of biological material comes into contact solely with a similar material, minimising abrasion due to friction.

The inner sheet of the sleeve is fixed to the outer sheet by suture stitches made with surgical thread possibly covered by a coating of biocompatible carbonaceous material substantially similar to that described previously with reference to the textile and to the suture stitches. The suture stitches (second suture stitches) extend along half moon-shaped paths. Each suture line defines a respective half moon edge of one of the three valve flaps of the prosthesis according to the invention. Preferably, the stitches are "straight" stitches co-extensive with the half moon path in the central part of the path itself and having a zig-zag course at the ends of this path.

The valve flaps have a generally bow-shaped configuration the manner in which the valve outwardly of the valve sleeve.

The manner in which the valve flaps are in a bow-shaped configuration. For the same purpose, but with less satisfactory results, other processes known to the expert in the art may be used.

Under rest conditions, the valve flaps converge inwardly of the sleeve, being disposed in an edge mating positing in the stellar configuration in which the convex faces and the concave faces of the flaps are visible.

The sheet also have a flared end collar portion which projects axially beyond the outer sheet. The collar portion is turned outwardly of the frame of the prosthesis, and is retained in the final assembled position by suture stitches which connect the end edge of the portion itself to the second sheet of the covering of biocompatible textile in correspondence with the radially inner edge of the upper face of the loop.

The function of the collar portion is to ensure that the end edge of the prosthesis upon which the blood flow impinges is completely covered by biological tissue with its antithrombogenic properties.

The radially innermost sheet of the sleeve is also fixed to the outer sheet in correspondence with apex parts of the appendages of the stent by further suture stitches each have a generally U-shape.

In particular, starting from a first and located outside the first sheet of the covering textile, the thread of each stitch penetrates one of the apertures and passes successively through the inner sheet of the covering textile, the outer sheet and the inner sheet of the sleeve. On the inner surface of the latter sheet, the thread forms a loop, from which the thread itself passes again this time in reverse order, through the inner sheet and the outer sheet of the sleeve and the inner sheet of the covering and then passes through the other apemare and the outer sheet of the biocompatible textile covering and emerges outside the prosthesis at another end. The configuration of the stitch described has been shown to be particularly advantageous both in terms of ease of formation and in terms of functional efficiency, reliability and structural strength. In particular, in the region of application of each stitch, the wall of the inner sheet is laid on the wall of he underlying outer sheet without giving rise to bends or folds which, in operation of the prosthesis, could act as starting points of ruptures or perforations in the biological tissue.

The suture stitches may be made with a thread having a coating of biocompatible carbonaceous material similar to that covering the stitches previously described.

With reference by way of example to an atrioventricular implant, in the diastolic phase, the blood which flows out of the atrium enters the ventricle by passing through the prosthesis. In this direction of flow, the blood impinges on the convex faces of the valve flaps, forcing their free edges apart and forming a central substantially cylindrical apemare in the body of the prosthesis through which the blood itself can flow freely. This apemare is defined in practice by the inner sheet of the valve sleeve. In particular, the manner of application of the stitches described previously ensures that there are no restrictions in the flow section for the blood at the outlet end of the prosthesis.

Immediately a pressure difference is established through the prosthesis as a result of the contraction of the ventricle inducing a flow of blood in the opposite direction, the pressure exerted by the blood itself on the concave faces of the valve flaps forces the free edges of these flaps into the mating position. Under these conditions blood flow through the prosthesis is prevented.

When the pressure gradient across the prosthesis again reverses as a result of the cardiac activity, the free edges of the flaps again diverge, allowing the free flow of blood. In some situations of operation the force exerted by the blood flow in opening the flaps may be very strong and cause the flaps to be projected rather violently against the inner surface of the frame. In the prosthesis according to the invention the harmful effect of this phenomenon is limited by virtue of the particular shaping of the stent and the markedly reduced axial extent of the tubular portion of the stent in the central region between the adjacent appendages. Thus in fact the extent of the frame portion against which the base region of the flaps may accidentally be projected is reduced to a minimum.

Still with regard to FIG. 2, it will again be noted that, for preference, the relative positions of fixing of the two sheets 10 and 12 is selected so that, when the tubular sleeve is closed into a tube, the inner sheet 12 (or functional sheet, this meaning the sheet which carries the valve leaflets 14) is made to project relative to the outer sheet in correspondence with the upstream edge of the prosthesis (or the input edge for the blood flow); all this facilitates the assembly on the valve stent.

The more recent prior art has made headway with yet another line of progress, that is to say, that of attempting to form cardiac valve prostheses without the need for a stent.

In other words one is dealing with valves termed "stentless" or "unstented", which do not have the rigid or substantially rigid annular structure present in most valves under current production.

In general, it may be said that a presence of a stent is in fact imperative in mechanical cardiac valve prostheses. One has, however, been made to appreciate that, in itself, the presence of a stent if not strictly necessary in biological valve prostheses: in particular, the fact that the valve prosthesis as a whole has good characteristics of deformability renders valves of this type, formed from biological material of valvular origin (that is, in practice, with the use of natural valves taken from animals—typically pig valves), particularly suitable for implantation by the surgeon because of functional advantages and, in particular, a greater similarity to the anatomy of natural aortic valves.

The present invention attempts specifically to make it possible to form stentless valves while avoiding the need to take cardiac valves from animals, and by constructing the valve prosthesis in accordance with an optimised design or model, not imposed by the anatomical configuration of animals which have considerable biological variations. All this may eventually make it possible to replace (either partially or completely) the natural biological tissue with a continuous, micro-porous and/or composite synthetic material (for example, polyurethane), with the result that it will be possible to replace the connection of the parts by stitching with connection by gluing or welding, or indeed by moulding the prostheses in a single piece.

According to the present invention, this object is achieved by means of a cardiac valve prosthesis having the characteristics claimed specifically in the claims which follow.

Figure 3:
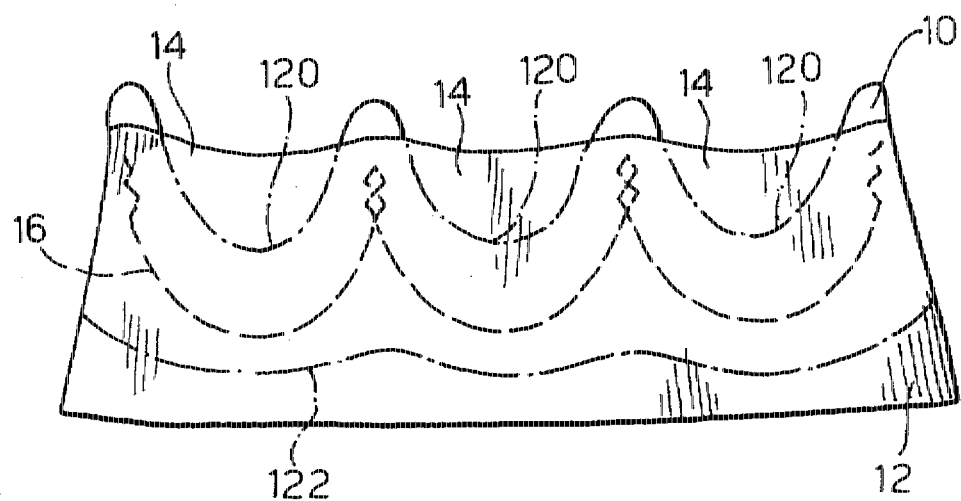
Figure 4:
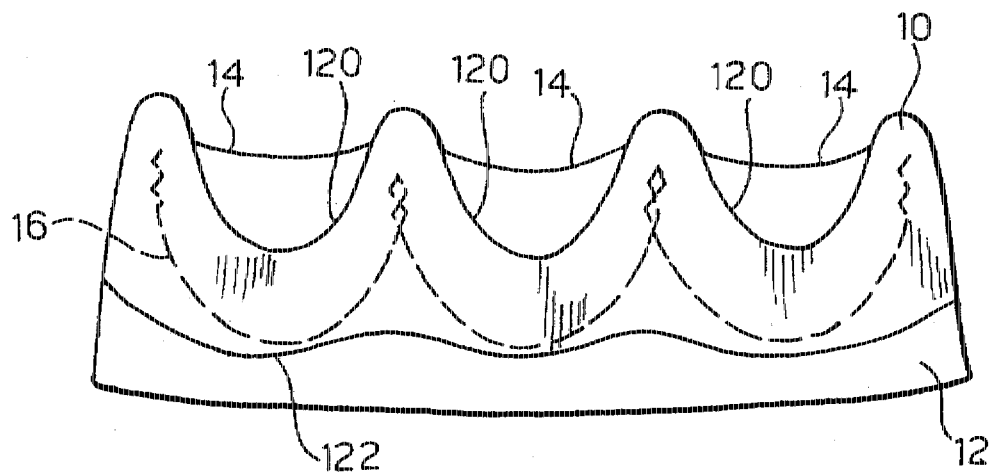
Figure 5:
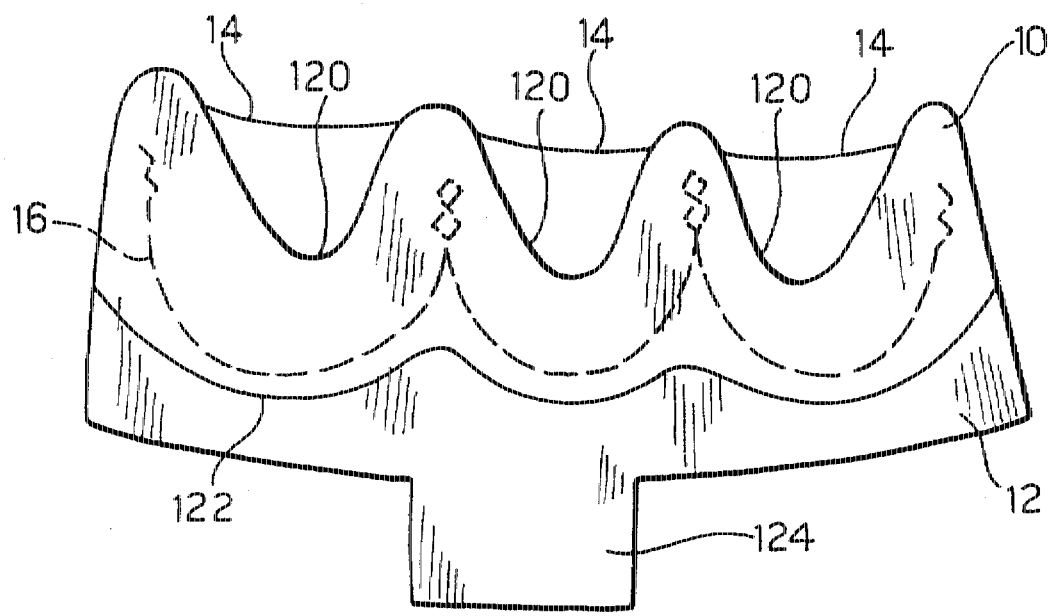
Figure 7:
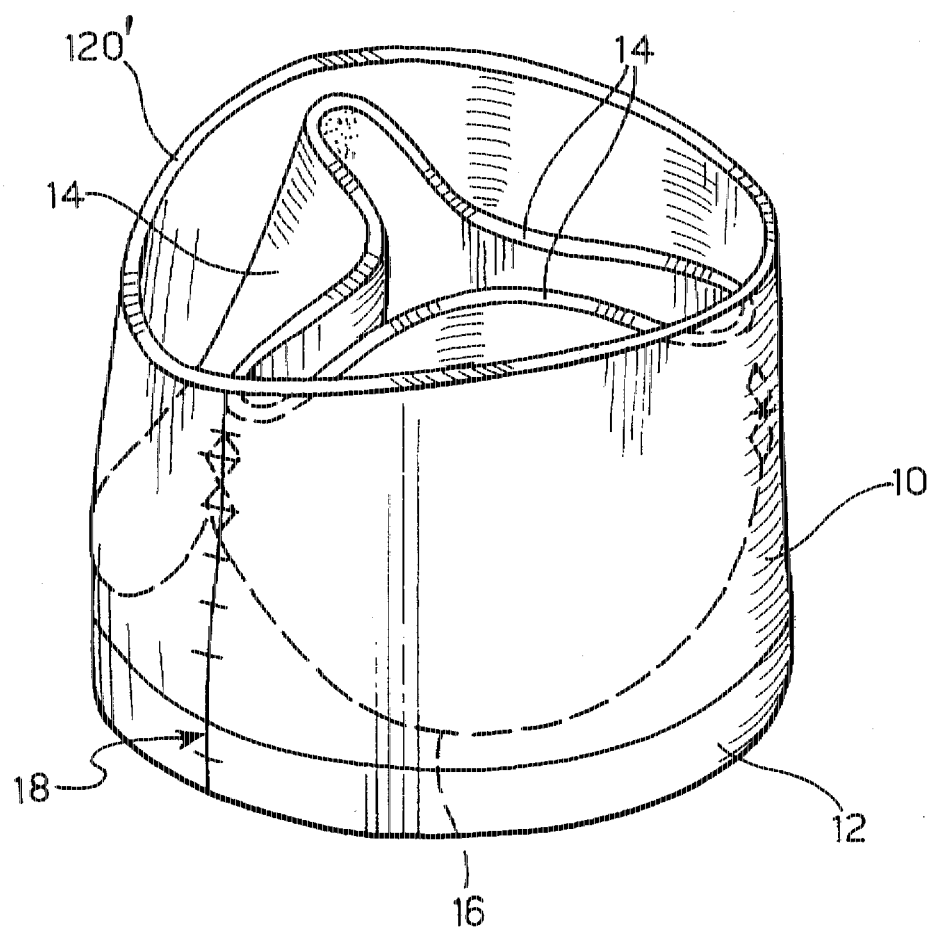
Figure 8:
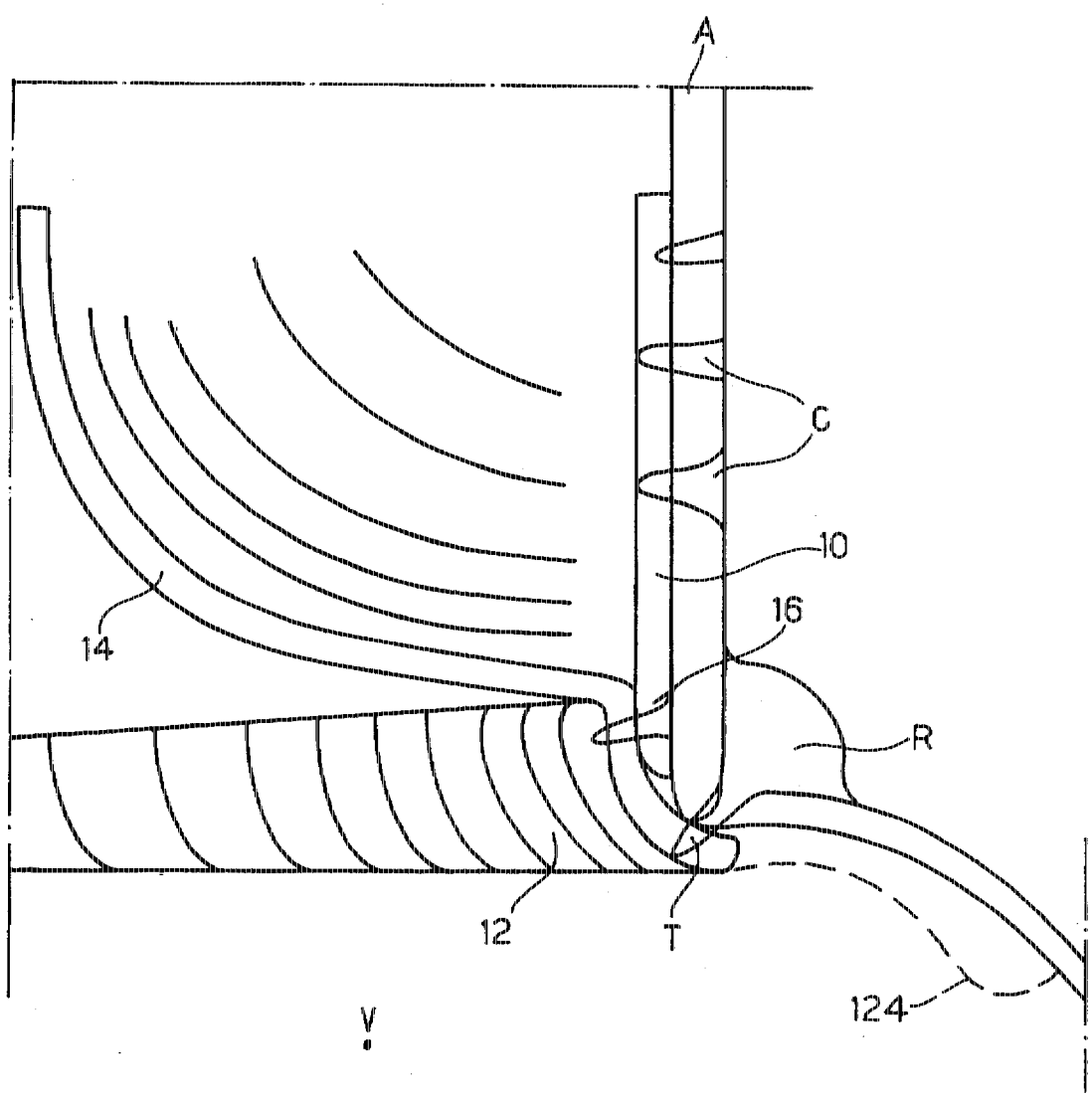

The invention will now be described, purely by way of non-limiting example, with reference to the appended drawings, in which:

FIGS. 1 and 2, which relate to the prior art have already been described above,

FIGS. 3 and 4 correspond substantially to FIG. 1 and illustrate the criteria for the manufacture of the valve sleeve of biological tissue in an aortic valve according to the invention, FIG. 5 illustrates a possible variant of a valve according to the invention, FIG. 6 illustrates the structure of the valve of the invention in its configuration of use, FIG. 7 is a view substantially similar to that of FIG. 6 illustrating a further possible variant of the invention, and FIG. 8 illustrates schematically the criteria of implantation of a valve of the invention.

In FIGS. 3 to 8 the same reference numerals already used in FIGS. 1 and 2 have been used to indicate parts functionally similar to those already described.

Thus, references 10 and 12 indicate respectively the outer and inner (or functional) sheets of biological material (or synthetic material, for example, polyurethane), while reference 14 indicates the halfmoon, sack-shaped parts formed in the latter which will form the valve leaflets of the prosthesis; finally, reference 16 indicates the line of festoon stitching (or welding or gluing) connecting the two sheets 10 and 12 along the outer edges of the valve leaflets 14, while reference 18 indicates the line of stitching along which the valve sleeve is closed into a tube.

An important characteristic of the solution of the invention lies in the fact that, in forming the edge of the outer sheet 10 intended to face the downstream end of the prosthesis, that is the outflow end with respect to the blood flow, this is not made to follow strictly the course of the line of festoon stitching 16, and hence the arcuate edges of the valve flaps 14, as it had in the prior art solution (FIG. 2).

In quantitive terms (without, however, wishing to attribute any limiting character thereto) one may state that, in the solutions adopted at present by the applicant in the manufacture of the solution described in the prior European patent EP-B-0155245, the edge 20 of the outer sheet 10 is cut at an approximately constant distance of the order of 2 mm from the festoon stitching 16.

On the contrary, in the solution of the invention shown in FIGS. 3 and 4, the homologous edge, indicated 120, is located as a certain distance from the arcuate edges of the valve flaps 14: in practice, at a distance of the order of about 1 cm from the festoon stitching 16. In general, the distance separating the edge 120 from the stitching 16 is not constant and has a minimum value in correspondence with the cusps of the festoon stitching 16 (for example, about 1 cm and a slightly greater value (for example, 1.2–1.5 cm) in correspondence with the loops of the stitching 16.

With reference to FIGS. 3 and 4, it will also be noted that the upstream edge of the outer sheet 10, indicated 122, is not completely straight but has a generally undulating shape which follows the course of the stitching 16 to a certain extent.

Again in the solution of the invention shown in FIGS. 3 and 4, and as already seen in the prior art solution, the arrangement of the relative fixing of the sheets 10 and 12 is selected so that, with the valve sleeve closed into a tube (see FIG. 6), the edge of the inner or functional sheet 12 facing the upstream end of the valve projects to a greater or lesser extent relative to the homologous edge of the outer sheet 10. As illustrated schematically in the variant of FIG. 5, this greater projection may, in effect take the form of an appendage 124 of the sheet 12, the position and dimensions of which can be varied selectively in dependence on specific applicational requirements so as to enable it to be sutured, for example, to the ventricular wall in a surgical reparatory operation. This appendage 124 of the sheet may, however, extend around the entire circumference of the prosthetic device in order to allow a repair or reinforcement of all or part of the annulus and/or of the adjacent ventricular wall.

In the further variant shown in FIG. 7, the downstream edge of the outer sheet 10 is not, in practice, subject to any cutting whereby the outer sheet 10 retains a generally rectangular shape (or slightly trapezoidal, for reasons which will be clarified below) so as to form a tubular jacket proper which surrounds the inner sheet 12 with the downstream edge (indicated 120') of the outer sheet 10 extending annularly and being substantially coplanar with the free edges (that is those which project inwardly of the valve orifice) of the valve leaflets 14. In a further variant (not illustrated) the edge 120 may be located at a certain distance downstream of the edge plane of the valve leaflets so as to form a prosthetic duct proper, giving the prosthesis as a whole the character of an aortic valve prosthesis.

As already stated, both with reference to the embodiments shown in FIGS. 3 to 5 and with reference to the variant of FIG. 7, the two sheets 10, 12 of biological material (and particularly the outer sheet 10, at least in its starting configuration) may be generally trapezoidal whereby, when the valve sleeve is closed on itself into a tube as illustrated in FIGS. 6 and 7, it is possible to give it a generally frusto-conical shape. This latter, as seen in the direction of the free flow of blood may be selected to be convergent or divergent depending upon the specific requirements for the implant.

In general, in all embodiments of the invention described, the extension of the outer sheet 10 for a certain distance beyond the line of festoon stitching 16 makes it possible to form a valve prosthesis constituted solely or substantially of biological tissue and, particularly, of biological tissue of non-valvular origin, without the support structure (armature or stent) of conventional valves. In other words, the invention enables a valve prosthesis of unstented type to be made without the need to make use of natural animal valves (for example, pigs' valves).

The valve according to the invention may be anchored firmly in the implant position, with all the advantages resulting from its intrinsic character of deformability, without this giving rise to functional problems.

FIG. 8 shows schematically how this is possible and relates to a possible implant position of a prosthesis according to the invention in replacing a natural, malfunctioning aortic valve. In FIG. 8, reference V indicates schematically the ventricle, while reference A indicates the aorta which extends from the so-called valve ring R of the ventricle V.

In cardiac operations for the replacement of the natural valve by a prosthetic valve, the structure and the strength of the ring R may often be compromised both by the removal itself, effected surgically, and by septic or non-septic increase in endocarditis. These degenerative phenomena may even extend to adjacent tissue to a certain extent.

By virtue of the axial extension of the outer biological sheet 10 relative to the valve (that is in the direction of flow of the blood) the valve according to the invention may be fixed firmly to the region of the ring and to the aortic wall with suture lines C so that, in addition to the necessary firm anchoring of the prosthesis in the implant site, it also repairs and consolidates the ring and the walls of the vessel. This effect may be made even more evident with the use of a solution such as that illustrated in FIG. 7, with the downstream edge 120' of the outer sheet 20 located at a certain distance from the end edges of the valve leaflets 14 so as to give the prosthesis as a whole the character of an aortic valve prosthesis.

In a complementary manner, the collar formed at the opposite end of the inner, or functional, sheet 12 may be fixed by further suture stitches T to the region of the ring R with a generally consolidating effect. Again, when appendages are present such as the appendage 124 in FIG. 5 it is possible to extend the repair even to the walls of the ventricle V when, for example, these have been damaged by endocarditis, or to provide for reconstruction of the ring.

Naturally, the principle of the invention remaining the same, the constructional details and forms of embodiment may be varied widely with respect to those described and illustrated without thereby departing from the scope of the present invention. This is particularly true with regard to the possibility, already indicated previously, of using a continuous, for example, micro-porous and/or composite synthetic material (for example, polyurethane) for the sheets 10 and 12 instead of natural biological tissue (for example, bovine pericardium). The use of this synthetic material has the potential advantage given by the possibility of replacing the connection by stitching of the sheets with connection by welding or gluing, a technique—the latter—which may possibly be applied even to biological tissue. In addition to this, recourse to synthetic materials also enables one to consider the possibility of making stentless prostheses in a single piece, for example, by moulding, instead of by the connection by separate sheets.

What is claimed is:

1. A stentless cardiac valve prosthesis adapted for implantation in a human body part and for having blood flow in a path therethrough from upstream to downstream, comprising:

a) an outer tubular member of biological tissue other than valvular tissue having an edge, wherein said edge of said outer member is adapted for attachment to the human body part in the downstream portion of the blood path; and b) an inner member connected to said outer member, wherein said inner member axially projects beyond said edge of said outer member, wherein said inner member has self supporting leaflets with arcuate edges and an extended portion, wherein said connection comprises at least one stitching line having a festoon course with loops following said arcuate edges of said leaflets and wherein said edge of said outer member is at least about 1 cm. from said festoon line, wherein said extended portion of said inner member is adapted for attachment to the human body part in the upstream portion of the blood path, wherein said leaflets are adapted to move between an open position and a closed position and form a conical shape when in the closed position and wherein said outer member and said inner member are stentless.

2. The prosthesis of claim 1, wherein said prosthesis comprises substantially non-valvular tissue.

3. The prosthesis of claim 1, wherein the prosthesis is selected from the group consisting of biological material and synthetic material.

4. The prosthesis of claim 1, wherein said extended portion of said outer member and said extended portion of said inner member extend a predetermined length for suturing the prosthesis to the body part during the implantation.

5. The prosthesis of claim 4, wherein said leaflets have arcuate edges, and wherein said outer member has homologous edges spaced a predetermined distance from said arcuate edges.

6. The prosthesis of claim 5, wherein said homologous edge has a generally festoon course following said arcuate edges of said leaflets.

7. The prosthesis of claim 5, wherein said homologous edge is generally straight.

8. The prosthesis of claim 25, wherein said homologous edge is spaced at least about 1 cm from said arcuate edges of said leaflets.

9. The prosthesis of claim 4, wherein said inner member projects a predetermined distance upstream of said edge of said outer member.

10. The prosthesis of claim 4, wherein said inner and outer members are formed from a generally trapezoidal shape.

11. The prosthesis of claim 3, wherein said synthetic material is selected from the group of materials having continuous, micro-porous, and composite properties and combinations thereof.

12. The prosthesis of claim 3, wherein said synthetic material is polyurethane.

13. The prosthesis of claim 4, wherein the connection between said inner and outer members is selected from the group consisting of stitching, welding, and gluing and combinations thereof.

* * * * *